United States Patent [19]
Lisa et al.

[11] Patent Number: 5,589,438
[45] Date of Patent: Dec. 31, 1996

[54] DRY FLOWABLE POWDERS OF HYGROSCOPIC PLANT GROWTH REGULATORS AND TABLETS FORMED OF THE SAME

[75] Inventors: Rudolph E. Lisa, Riverview; Terence K. Kilbride, Bloomfield Hills, both of Mich.; Karl-Friedrich Jager, Lumburgerhof, Germany

[73] Assignee: BASF Corporation, Mt. Olive, N.J.

[21] Appl. No.: 415,124

[22] Filed: Mar. 30, 1995

Related U.S. Application Data

[62] Division of Ser. No. 95,122, Jul. 20, 1993, Pat. No. 5,468,720.

[51] Int. Cl.[6] .......................... A01N 25/12; A01N 43/40; A01N 43/58

[52] U.S. Cl. .................. 504/236; 504/248; 71/DIG. 1

[58] Field of Search ................. 504/116, 236, 504/248; 71/DIG. 1

[56] References Cited

U.S. PATENT DOCUMENTS

| | | | |
|---|---|---|---|
| 3,356,569 | 12/1967 | Nicodemus et al. | 167/55 |
| 3,905,798 | 9/1975 | Zeeh et al. | 71/76 |
| 4,134,725 | 1/1979 | Büchel et al. | 8/79 |
| 4,999,041 | 3/1991 | Grossmann et al. | 71/70 |
| 5,294,594 | 3/1994 | Kimler et al. | 504/116 |

*Primary Examiner*—S. Mark Clardy
*Attorney, Agent, or Firm*—Nixon & Vanderhye P.C.

[57] ABSTRACT

The present invention provides hygroscopic plant growth regulator formulations in solid forms and associated methods of making the powders and tablets. The most preferred formulation uses an effective amount of an N,N-dimethylpiperidinium salt such as mepiquat chloride.

20 Claims, 3 Drawing Sheets

DRY FLOWABLE POWDERS OF HYGROSCOPIC PLANT GROWTH REGULATORS AND TABLETS FORMED OF THE SAME

This is a divisional of application Ser. No. 08/095,122 filed Jul. 20, 1993 (now U.S. Pat. No. 5,468,720).

BACKGROUND OF THE INVENTION

1. Field of the Invention

The present invention relates to methods for making flowable, highly concentrated powders and tablets of hygroscopic plant growth regulator compounds, and more specifically to processes to dry mepiquat chloride aqueous solutions to form flowable highly concentrated solid products.

2. Background of the Prior Art

Plant growth regulators affect the physiology of plant growth and influence the natural rhythm of a plant. More specifically, plant growth regulators may, for example, reduce plant height, stimulate seed germination, induce flowering, promote or inhibit fog, darken leaf coloring, minimize lodging of cereals, slow grass growth on lawns, reduce boll rot and provide better boll retention in cotton.

Plant growth regulators may be applied to plants in a variety of methods including different formulations. Of these various methods, use of liquid and dry compositions are the most common. The particular formulation desired and resulting efficacy enhancement will greatly depend upon the species to be treated, environmental conditions, the geographical area and the climatology of the area at the time of treatment.

The plant growth regulator, known trivially as mepiquat chloride, is generally used to control various aspects of cotton boll growth. See, for example, Khafaga, Angew. Botanik 57, 257–265 (1983); Sawan et al., J. Agronomy & Plant Science, 154, 120–128 (1985); U.S. Pat. Nos. 3,905,798 and 4,447,255.

Mepiquat chloride is used as a plant growth regulator in agriculture. Mepiquat chloride has a high water solubility of more than 600 g/L. The melting point is 223° C. The substance is very hygroscopic, readily absorbing moisture from humid air, so much so, that the dry powder can turn to liquid when exposed to ambient humid air. During Storage, .the solid mepiquat chloride readily cakes and sticks container surfaces, even at low residual water contents of less than 0.5%.

These properties make it extremely difficult to dry mepiquat chloride. In conventional spray dryers, the material is very difficult to dry. It must be atomized extremely finely to reduce the moisture to a suitable level and even then it retains too much water to dry practically. The product remains sticky and adheres to the walls of the dryer and the dryer ducts and cyclones, eventually plugging the ducts and cyclones. Furthermore, powder from such a process, because it is so fine, flows poorly out of the dryer, and upon storage in a drum, is rendered unflowable due to caking.

Solid forms of plant growth regulators offer a number of key advantages, including convenience, increased stability and shelf life, as well as reduced packaging, storage and shipping costs. Additionally, there is the possibility of future government regulation requiring solid forms of agricultural products in order to reduce handling of contaminated packaging of these products during field application and during disposal. These dry flowable plant growth regulating compounds would be safer for the farmer to use and dispose of, and also result in a smaller volume of hazardous waste being produced.

There is a need for dry, flowable, highly concentrated powder and tablet formulations of hygroscopic plant growth regulators.

SUMMARY OF THE INVENTION

Surprisingly, a free-flowing, non-caking solid mepiquat chloride formulation can be achieved by mixing the solid hygroscopic plant growth regulator with finely divided, highly absorptive inerts. In such mixtures, concentrations of the plant growth regulator of up to about 99 percent by weight are achievable. When the mixtures of the invention are directly applied in a spray tank, the plant growth regulator dissolves instantly in the water without residues.

The preferred plant growth regulators of the present inventions include the group consisting of 1,1-dimethyl-3,4-dehydropiperidinium bromide, 4-chloro-1,1-dimethyl piperidinium bromide, 1,1-dimethylhexahydropyridazinium bromide, and 1,1-dimethylpiperidinium chloride, also known as mepiquat chloride.

It is an object of the present invention to provide an agriculturally acceptable hygroscopic plant growth regulator formulation in a solid form.

It is a further object of the present invention to provide methods of making the solid form of hygroscopic plant growth regulator compositions of the present invention, It is another object of the present invention to provide an agriculturally acceptable hygroscopic plant growth regulator formulation in the form of a tablet.

It is a further object of the present invention to provide methods of making the dry, flowable tablet form of hygroscopic plant growth regulator compositions of the present invention.

These and other objects of the present invention will be more fully understood from the following description of the invention.

DETAILED DESCRIPTION OF THE PREFERRED EMBODIMENTS

Figure 1:
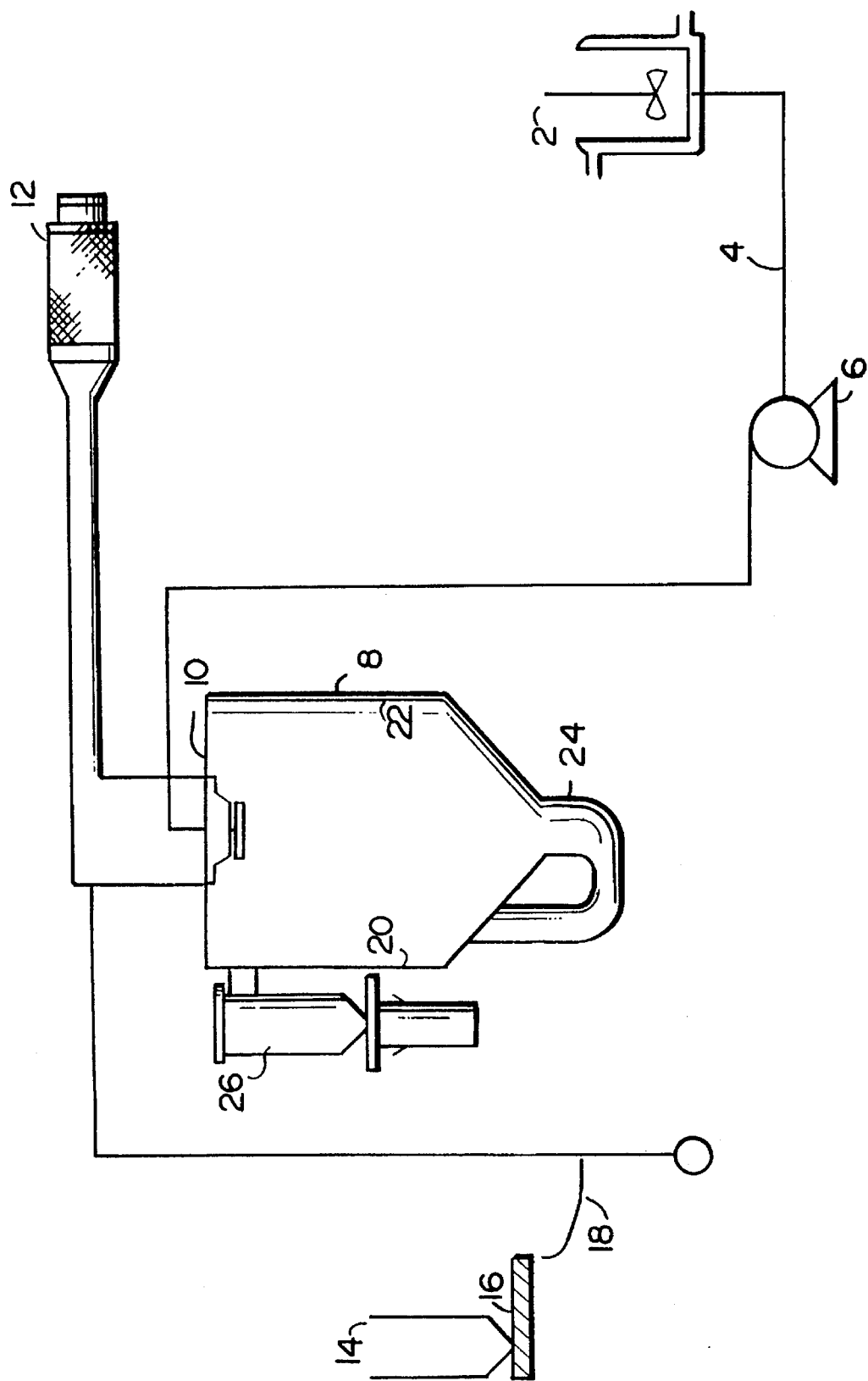
FIG. 1 illustrates a spray dryer used in a method of the present invention.
Figure 2:
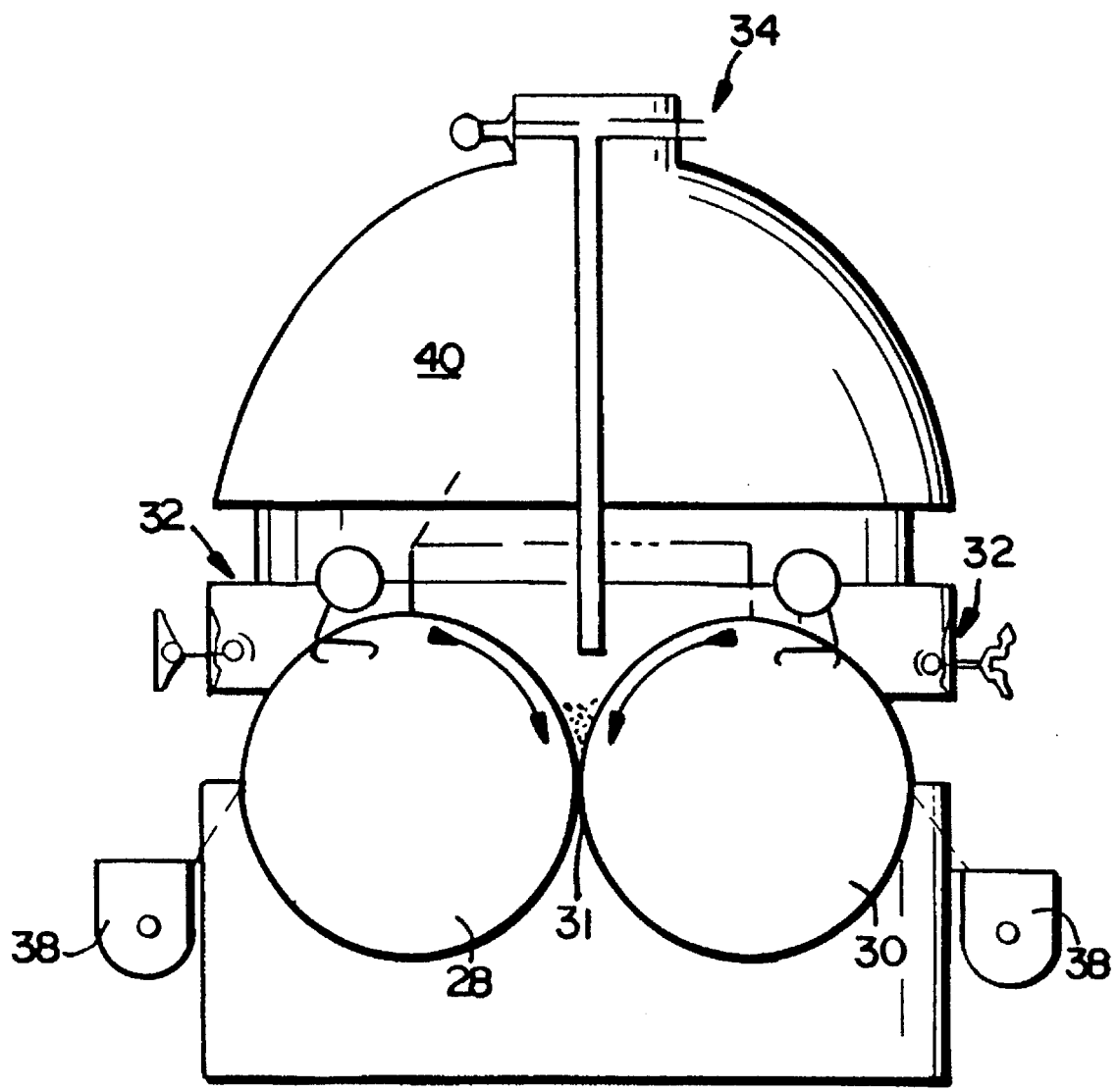
FIG. 2 illustrates a double drum dryer used in a method of the present invention.
Figure 3:
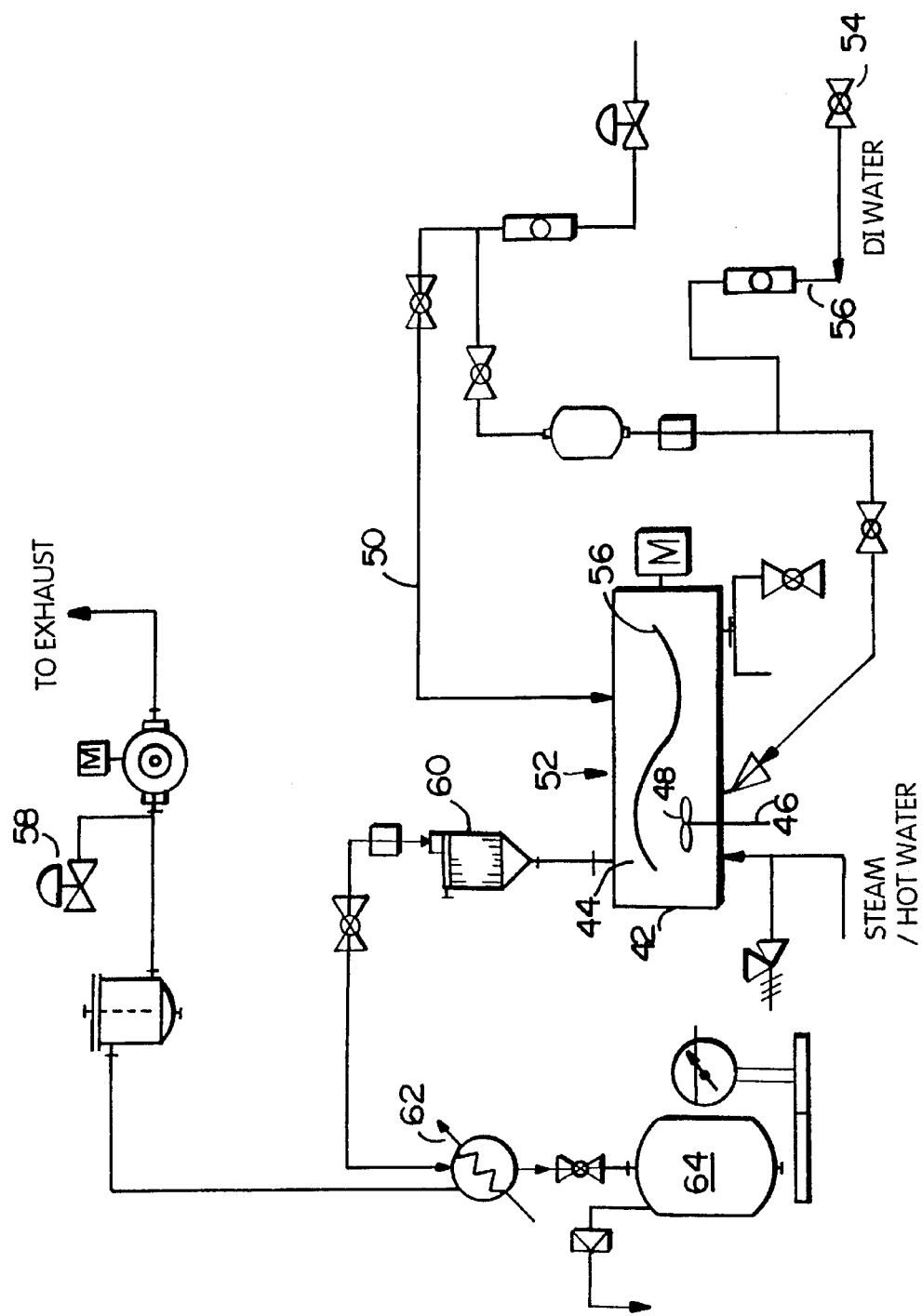
FIG. 3 illustrates a batch vacuum dryer used in a method of the present invention.

As used herein, the term "agriculturally acceptable" includes agricultural, industrial and residential use.

As used herein, "plant growth regulator(s)" (hereinafter abbreviated as "PGR") or "regulation" includes the following plant responses: inhibition of cell elongation, for example reduction in stem height and internodal distance, strengthening of the stem wall, thus increasing the resistance to lodging; compact growth in ornamentals for the economic production of improved quality plants; promotion of better fruiting; increasing the number of ovaries with a view to stepping up yield; promotion of senescence of the formation of tissue enabling fruit to absciss; defoliation of nursery and ornamental bushes and trees for mail-order business in the fall; defoliation of trees to interrupt parasitic chains of infection; hastening of ripening, with a view to programming the harvest by reducing the harvest to one to two pickings and interrupting the food-chain for injurious insects.

As used herein, PGR formulation of the present invention may be used to form both package and tank mix compositions.

The present preferred invention comprises PGR compositions comprising an agriculturally and plant growth regulating effective amount of a hygroscopic PGR, and more preferably, an N,N-dimethylpiperidinium salt in a dry flowable highly concentrated powder.

Preferred PGRs include salts of the formula:

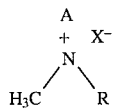

where R is methyl or ethyl; X is the anion of an inorganic or organic, but not phytotoxic acid, preferably bromide or chloride, and A is a chain of 4 or 5 methylene groups, which chain may be substituted by chloro, bromo, methyl, chloromethyl, bromomethyl, hydroxymethyl, and methylene, or which chain containing one or two double bonds, or A is the chain $-(CH_2)_n-NH-$, where n is 3 or 4, disclosed in U.S. Pat. No. 3,905,798 and hereby incorporated by reference.

Preferred specific examples of PGRs include 1,1-dimethyl-3,4-dehydro-piperidinium bromide, 4-chloro-1,1-dimethyl- piperidinium bromide, 1,1-dimethylhexahydropyridazinium bromide and 1,1-dimethyl-piperidinium chloride. The most preferred plant growth regulator is 1,1-dimethyl-piperidinium chloride, also known as N,N-dimethylpiperidinium chloride or mepiquat chloride. This product is commercially available under the registered trademark Pix® (BASF AG, Germany).

For convenience of description, mepiquat chloride will be used. However, the methods described apply equally to other hygroscopic PGRs.

In a preferred embodiment, silica is injected in the inlet air stream of a spray dryer at a controlled rate.

A spray dryer of the type illustrated in FIG. 1 may be used. As can be shown from FIG. 1, the aqueous PGR feed solution is agitated in a feed tank (2) and fed through a line (4) via a feed pump (6) into the spray dryer unit (8). The aqueous PGR feed solution is introduced into the spray dryer unit by an atomizing means (10). An inlet air heating means (12) provides heat to the dryer at a temperature of about 150 to about 250 degrees °C.

A flow aid such as silica is stored in a feed hopper (14) and injected into the spray dryer unit (8) via a screw feeder (16) through a line by an air eductor (18). The silica adheres to the forming droplets or partially dried particles formed by the aqueous mepiquat chloride feed solution in the vicinity of the atomizer (10) and reduces or eliminates the tendency of the partially dried mepiquat chloride particles from sticking to the spray drying unit walls (20, 22), the ducts (24), and the cyclone (26). The silica also renders the powder more flowable, eliminating caking in the drum even when stored for long periods of time provided the drum excludes ambient moist air. The flowing powder is then suitable for commercial tabletting or for filling water soluble bags.

The rate at which the aqueous PGR feed solution is fed into the spray dryer unit is not critical and is dependent upon the size of the spray dryer used. This rate is easily determined by those skilled in the art.

A preferred method dries the mepiquat chloride solution with a double drum dryer as illustrated in FIG. 2. The double drum dryer has a pair of hollow, rotating drums (28, 30) whose surfaces are scraped by a respective knife (32). High pressure steam is introduced to the interior of the drums and mepiquat chloride solution added continuously via a feed line (34) to the nip between the drums (36). The drums turn toward one another, by means of a conveyor, for example 38 depositing a portion of the liquid, boiling mepiquat chloride solution on the drum surface (28, 30) where boiling is initiated. Upon further rotation, the thin film of mepiquat chloride's water boils off into the vapor hood (40) and a solid film remains that is scraped by sharp knives (32) from the turning drum surface (28,30). The material is then collected and the flow aid is added to it to improve flowability and impart anti-caking properties prior to tabletting or filling water soluble bags.

A preferred embodiment of the drying process utilizes a batch vacuum dryer with chopping blades which can also be described as a mechanical fluid bed. The most preferred batch vacuum dryer is a Littleford® type (or Lödige) vacuum dryer, as illustrated in FIG. 3.

As is seen from FIG. 3, the vacuum dryer unit (50) consists of double jacket (42, 44). Inside the double jacket is a hollow rotating shaft (46) with attached plough shaped mixing elements (48).

Aqueous PGR feed solution is fed via a line (50) into the vacuum dryer unit (52). Steam or hot water (54) is fed via a line (56) into a jacket (42) which surrounds the vacuum dryer unit (52), and optionally through the hollow rotating shaft (46). Agitating means (56) in the interior of the vacuum dryer unit (52) agitates the aqueous PGR feed solution. A vacuum means (58), which may be a pump or vacuum jet unit is introduced into and applied to the vacuum dryer unit (52). The vacuum and applied jacket heat causes the evaporation of the water from the aqueous PGR feed solution. The evaporated water boils up, passes through a bag collector means (60), and is recovered by a condenser (62) and collected in a condensate tank (64).

When a sufficient amount of water has been evaporated, a paste begins to form. Mixing elements (48) are used to divide the paste, breaking it up, and bringing the interior moisture to the surface so as to expose it to the vacuum to increase the drying rate. As the material solidifies, the chopping means breaks the material into small particles to maintain the high drying rate.

A free-flowing, non-caking solid mepiquat chloride formulation can be achieved by mixing the solid mepiquat chloride with a finely divided, highly absorptive inert flow aid such as silica. The addition of silica or other flow aid renders the powder flowable and non-caking, and suitable for tabletting or filling water soluble bags. The flow aid is introduced manually or mechanically through a port on or near the top of the drying chamber.

All three drying processes use silica or other flow aid to improve flowability and prevent caking. These inert additives include any form of silica including fumed silicas, precipitated silicas, aluminum silicates, magnesium silicates, and the like, zeolites, bentoinites, montmorillonites, and attapulgites and mixtures thereof. The most preferred silica is commercially available as Sipernat® 50S.

The weight of silica per weight of mepiquat chloride in all of these drying processes is about 0.2:100 to 3:100, and more particularly, about 2:100.

Optionally, to further improve flowability, reduce sticking tendancy or caking, or to increase the dissolution rate, binders, fillers, and/or disintegrants can be dissolved in the feed solution before drying. Suitable binders, fillers, and/or disintegrants include water-soluble cellulose derivatives, cellulose derivatives, carboxymethyl cellulose, hydroxypropyl methylcellulose, water soluble gums such as gum arabic, gum tragacanth, alginates, gelatin, and polyvinylpyrollidone, cross-linked polyvinylpyrollidone, microcrystalline cellulose, modified starches such as sodium carboxymethyl starch, and mixtures thereof.

Other suitable fillers, binders, and/or disintegrants include any water soluble starch, corn syrup, dextrin or pregelatinized starch which is at least partially soluble in water at ambient temperature. For example, there can be used as a binder the pregelatinized, modified and stabilized waxy maize starch which is marketed by the National Starch and Chemical Corporation under the trade name Instant Celar Gel. In addition, pregelatinized corn starch marketing by the Hubinger Company under the trade name OK Pre-Gel can be used. Other binders suitable for use are pregelatinized food starch, refined from tapioca and marketed under the trade name Instant Gel; stable, modified amylopectin marketed under the trade name Kosol; a low viscosity tapioca dextrin marketed under the trade name Crystal Gum; dextrinized corn starch marketed under the trade name Purity Glaze; maltodextrin marketed under the trade name Maltrin, such as M040 by Grain Processing Corporation.

All of the above-described powders, with and without fillers, binders, and/or disintegrating agents can then be tabletted or filled into water soluble bags. Unexpectedly, the high potency powders which contain only the hygroscopic PGR active material and silica flow aid, tablet without aid of binders, fillers, and/or disintegrants, or lubricants on a commercial tablet press. The tablets formed are of commercial quality, having reproducible weight, sufficient tablet strength, and acceptable solubility. Water absorbance is minimal provided that the tablets are made in a dehumidified room. The tablets can be dissolved and passed through a 50 mesh screen such as that found on spray equipment without residue.

While the ratios of the concentrations of the various components of the present invention hereinafter suggested, those skilled in the art will recognize that minor variations may be necessary to accommodate particular characteristics of acceptable plant growth regulators which may be employed in this invention.

In general, the formulations of the present invention contain from about 0.1 to about 99.8%, and preferably from about 95 to about 99% by weight of active ingredient.

Typically, for a plant growth regulator concentrate of the present invention, the concentration of regulator active ingredient will be at least 0.0125 pints/acre.

In such mixtures, concentrations of mepiquat chloride up to about 99 percent by weight are achievable. When the mixtures of the invention are directly applied in a spray tank, the mepiquat chloride dissolves instantly in the water and this spray solution passes a 50 mesh screen of the spray equipment without residues.

The tablets can be manufactured by compressing the mixtures on tablet machines. Also for tabletting, other inert ingredients like disintegrants, binders, fillers, and/or disintegrants, wetting agents or lubricants can be blended with the PGR mixture. (Optionally, the wetting agents and lubricants can be incorporated by addition in the drying step-either into the PGR liquid solution before drying, or can be added with the inert flow aid during drying.)

When the tablets are dropped into the water of the spray tank, the mepiquat chloride is quickly dissolved and this spray solution passes a 50 mesh screen of the spray equipment without residues.

In addition to the above-described components, the compositions of the present invention may also include other ingredients or adjuvants commonly employed in the art.

Examples of such ingredients include drift control agents, defoaming agents, preservatives, surfactants, fertilizers, phytotoxicants, herbicides, pesticides, insecticides, fungicides, wetting agents, adherents, nematocides, bactericides, trace elements, synergists, antidotes, mixtures thereof and other such adjuvants well known in the plant growth regulator art.

However, it is preferred to employ the compositions of the present invention along with sequential treatments with these other components for optimal effect.

The compositions of the present invention may be applied to plants. The application of liquid and particulate solid plant growth regulator compositions to above ground portions of plants may be carried out by conventional methods, for example, boom and hand application, including sprayers or dusters. The composition may be applied aerially as a spray, if desired. The mixtures of the present invention are preferably used in the form of aqueous solutions. The mixtures are applied in a conventional manner, for example, by spraying, atomizing, watering or disinfecting seed.

The forms of application depend entirely on the purpose for which the compositions are being used. In any event, they should ensure a fine distribution of the active ingredients in the composition.

The above plant growth regulator formulation may then be dispersed in water and sprayed onto plants according to the method of the present invention.

Powders, dusts and broadcasting agents may be prepared by mixing or grinding the active ingredients with a solid carrier.

Granules, for example, coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, and the like.

The action of the compositions of the present invention are optimal even at low application rates. For a given plant growth regulator composition, the skilled artisan will readily arrive at a composition having the optimum ratio of the ingredients by routine experimentation.

The compositions of this invention may be prepared, for example, by adding, in any order, the various components of the composition of the present invention. For example, one may start with a commercial formulation of mepiquat chloride, which is an aqueous concentrate containing 0.35 pounds per gallon of mepiquat chloride (4.2%) by weight. Thereafter, in any order, one mixes suitable amounts of any optional adjuvants or ingredients.

The following examples serve to illustrate the invention and should in no way be construed as limiting the scope thereof.

EXAMPLES

Example 1 - Formulation

An aqueous solution of mepiquat chloride was dried to give a solid mepiquat chloride with a water content of 0.2%.

This product was not free flowing and caked in a sealed, tight container after 2 days of storage at room temperature.

Directly after drying, 198 g solid mepiquat chloride were mixed with 2 g of Aerosil® 200 in a laboratory mixer to give a homogeneous mixture. After storage in a sealed container for 1 month at room temperature and 50° C., there was no caking. The mixture remained free flowing. Twenty grams of the mixture were poured into a laboratory spray tank filled with 1 gallon tap water at room temperature. The mepiquat chloride dissolved completely within 1 minute. There was no residue on a 100 mesh screen of the laboratory spray tank.

Example 2 - Water Soluble Bag

One hundred grams of the mixture described in Example 1 were packaged using a water soluble film (Monosol® M7030). This water soluble bag was dropped into a spray tank filled with 25 gal. tap water at room temperature. The water was circulated through a 50 mesh screen. The mepiquat chloride and the film of the bag dissolved completely within 10 minutes. These was no residue on the 50 mesh screen.

Example 3 - Tablet Formulation

Ninety-five grams of the mixture described in Example 1 and 5 g Divergan® F were blended in a laboratory mixer. A 15 g tablet, 2½ in. (5.7 cm) diameter, was made with a hand operated hydraulic press. The tablet was dropped into a spray tank with tap water at room temperature. The tablet broke up completely and the mepiquat chloride dissolved within 10 minutes. There was no residue on the 50 mesh screen of the spray tank.

Example 4 - Formulation

Directly after drying as described in Example 1, 294 g solid mepiquat chloride were mixed with 6 g Sipernat® 50 S in a laboratory mixer to give a homogeneous mixture. After storage in a sealed container for 1 month at room temperature and 50° C., there was no caking. The mixture remained free flowing.

Twenty grams of the mixture were poured into a laboratory spray tank filled with 1 gal. tap water at room temperature. The mepiquat chloride dissolved completely within 1 minute. There was no residue on the 100 mesh screen of the laboratory spray tank.

Example 5 - Water Soluble Bag

One hundred grams of the mixture described in Example 4 were packaged using a water soluble film (Mono Sol® M8532). This water soluble bag was dropped into a spray tank filled with 25 gal. tap water at room temperature. The water was circulated through a 100 mesh screen. The mepiquat chloride and the film dissolved completely within 10 minutes. These was no residue on the 100 mesh screen.

Example 6 - Tablet Formulation

Using the mixture of Examples 4, 20 g tablets, 2½ in. (5.7 cm) diameter, were made with a hand operated hydraulic press. Five tablets were dropped into a spray tank filled with 25 gal. tap water at room temperature. The tablets broke up completely and the mepiquat chloride dissolved within 12 minutes. There was no residue on the 100 mesh screen of the spray tank.

Example 7 - Formulation

A 600 g/L solution of mepiquat chloride was placed in an agitated, jacketed, spray dryer feed tank and heated to 65° C. with tempered water. The heated solution was pumped at 125 g/min to an atomizing wheel rotating at about 17,000 rpm in a Niro Utility spray dryer. Silica (Sipernat 50S) from a loss-in-weight screwfeeder was injected via an air eductor into the air plenum to mix with the heated air entering the plenum. The silica was fed at a rate of 4% based on the dry basis feed rate of the mepiquat chloride solution. The silica/air mixture, at 200° C., then entered the drying chamber, intermixing with the droplets formed by the atomizer. The resultant outlet temperature is about 140° C. On drying the powder exits the drying chamber does not adhere to the walls of the spray dryer, the ducting, or the cyclone separator. The powder remains flowable in a polyethylene bag packed in a sealed plastic drum.

The resulting powder was flowable, had a moisture content of 0.25%, a bulk density of 0.29 g/ml untapped, 0.38 g/ml tapped, and an ash content of about 2%. The powder assayed at about 97% mepiquat chloride.

Example 8

Steam at 105 psig was introduced to a lab scale double drum dryer and the rolls rotated at about 5 rpm. Mepiquat chloride liquid was fed from a reservoir to the nip of the rolls at a rate of about 36 g/minute. The material adhered to the rolls and the moisture was evaporated while the drums rotated. The solid film was scraped off the rolls by a blade and collected. Material collected without silica rapidly caked. Material that was collected and mixed with about 2% (Sipernat 50S) silica did not cake and was flowable. The moisture content was about 1.2% in the resultant powder, with a density of 0.25 g/ml untapped and 0.35 g/ml tapped.

Example 9

To a 130 liter Littleford "mechanical fluid bed" dryer (Model FKM-130 with chopping blade), 171.6 lbs of mepiquat chloride 600 g/L aqueous solution was charged. The agitator plough was started at 155 rpm, and 15 psig steam introduced to the jacket. A vacuum was pulled with a vacuum pump, maintaining 600 mm Hg at the pump. The evaporated vapors passed through a bag filter and were condensed using a cold glycol/water mixture on the shell side of a condenser. The resulting condensate was collected in a receiver. As evaporation continued, the amperage drawn by the plough motor began to rise. The chopper blades were turned on, and the drying completed. During this time the steam pressure on the jacket was progressively increased to drive off the water from the forming paste. As more water was removed, the paste turned to solid, the chopper greatly increasing the rate of drying by dividing moist material and exposing the interior moisture to the vacuum and hot dryer walls. When water was no longer being removed, the dried solid was cooled by applying cool water to the jacked of the apparatus. Approximately 2% of silica was then added to the material and allowed to blend. When this mixing operation was complete, the finished product was discharged to a drum.

The resulting free flowing powder was composed of particles ranging from approximately 5 to 60 microns in diameter, with a moisture of about 0.08%, and bulk density of 0.63 untapped and 0.79 tapped, and ash content of about 2%. The powder assayed at about 97% mepiquat chloride. There was no detectable mepiquat chloride in the overhead condensate.

Example 10

About 10 pounds of powder made by the method in Example 9 was charged to the feed hopper of a single station Stokes R excenter tablet press located in a low humidity room. The relative humidity of the room remained about 28% between 70° and 80° F. The press was fitting with tooling to make 2.25 inch diameter tablets. After pressure and size adjustments, tablets were made of about 21 grams with good tablet integrity. Hardnesses, as measured on a RIMAC tester, were 15 to 21 lbs force. Tablets were found to have picked up less than 0.3% moisture during this operation.

The tablets had thicknesses of about 0.8 to 0.9 centimeters. The tablets dissolved under mild agitation in water in about 7 to 9 minutes and the resulting liquid did not deposit any residue when passed through 150 micron sieve (100 mesh).

Whereas particular embodiments of the invention have been described above for purposes of illustration, it will be appreciated by those skilled in the art that numerous variations of the details may be made without departing from the invention as described in the appended claims.

Example 11

A mepiquat chloride powder prepared by the method of (example 8 for drum dryer) was tabletted in a Carver press. Press pressure was varied at 6 to 7 metric tons, 8 to 9 metric tons, and 10 to 11 metric tons for durations of 1 minute each. The formed tablets, of 2.26 inches in diameter, had thicknesses between 0.24 and 0.26 inches with weights of between 15.3 to 15.6 gms, with breaking strengths between 9 and 22.3 lbs as determined on a modified Chatilion electronic tester, model DFI-50 mounted on a model LTC manual test stand. The tablets were dissolved in 750 ml of 342 ppm hardness water stirred with a magnetic stirring bar and dissolved completely in 0.9 to 4.7 minutes.

Example 12

A mepiquat chloride powder prepared by the method of (example 9 for the Littleford dryer) was tabletted in a Carver press. Press pressure was varied at 8 to 9 metric tons, and 10 to 11 metric tons for durations of 1 minute each. The formed tablets, of 2.26 inches in diameter, had thicknesses between 0.24 and 0.26 inches with weights of between 15.3 to 15.7 gms, with breaking strengths between 17 and 32 lbs as determined on a modified Chatilion electronic tester, model DFI-50 mounted on a model LTC manual test stand. The tablets were dissolved in 750 ml of 342 ppm hardness water stirred with a magnetic stirring bar and dissolved completely in 4.4 to 5.8 minutes.

Example 13

A mepiquat chloride powder prepared by the method of (example 7 for the spray dryer) was tabletted in a Carver press. Press pressure was varied at 6 to 7 metric tons, 8 to 9 metric tons, and 10 to 11 metric tons for durations of 1 minute each. The formed tablets, of 2.26 inches in diameter, had thicknesses between 0.23 and 0.28 inches with weights of between 14.4 to 15.7 gms, with breaking strengths between 16.5 and 55 lbs as determined on a modified Chatilion electronic tester, model DFI-50 mounted on a model LTC manual test stand. The tablets were dissolved in 750 ml of 342 ppm hardness water stirred with a magnetic stirring bar and dissolved completely in 3.8 to 4.8 minutes.

Whereas particular embodiments of the invention have been described above for purposes of illustration, it will be appreciated by those skilled in the art that numerous variations of the details may be made without departing from the invention as described in the appended claims.

What is claimed is:

1. A dry, flowable powder of a plant growth regulator formulation comprising a mixture of (i) a solid particulate consisting essentially of at least 95% by weight of a hygroscopic plant growth regulator, and (ii) an effective amount between 0.2 to 3 parts by weight per 100 parts by weight of the plant growth regulator of an inert flow aid sufficient to inhibit hygroscopicity of said plant growth regulator such that said powder remains free-flowing and non-caking.

2. The formulation of claim 1 wherein said plant growth regulator is an N,N-dimethyl-piperidinium salt.

3. The formulation of claim 2 wherein said plant growth regulator is selected from the group consisting of 1,1-dimethyl-3,4-dehydropiperidinium bromide, 4-chloro-1,1-dimethylpiperidinium bromide, 1,1-dimethyl-hexahydropyridazinium bromide, and 1,1-dimethylpiperidinium chloride.

4. The powder of claim 1, wherein said plant growth regulator is mepiquat chloride.

5. The powder as in claim 1, wherein the inert is selected from the group consisting of silicas, fumed silicas, precipitated silicas, aluminum silicates, magnesium silicates, zeolites, bentonites, montmorillonites, attapulgites, and mixtures thereof.

6. The powder of claim 1, wherein the dry, flowable powder comprises fillers, binders and/or disintegrants.

7. The powder of claim 6, wherein the fillers, binders and/or disintegrants are selected from the group consisting of water-soluble cellulose derivatives, cellulose derivatives, carboxymethyl cellulose, hydroxypropyl methylcellulose, water-soluble plant gums, alignates, gelatin, polyvinylpyrolidone, water-soluble starch, corn syrup, dextrin, pregelatinized starch which is at least partially soluble in water at ambient temperature, pregelatinized food starch, stable modified amylopectin, a low viscosity tapioca dextrin, dextrinized corn starch, maltodextrin microcrystalline cellulose, crosslinked polyvinyl pyrollidone, sodium carboxymethyl starch, and mixtures thereof.

8. The powder of claim 6, wherein the fillers, binders and/or disintegrants are carboxymethylcellulose.

9. The powder of claim 6, wherein the fillers, binders and/or disintegrants are present in an amount of about 0.1%.

10. The powder of claim 1, wherein the mixture further comprises fillers, binders and/or disintegrants which are present in a ratio of the plant growth regulator to the fillers, binders and/or disintegrants of about 99.7:0.1.

11. A tablet formed of a compressed powder of a plant growth regulator formulation which comprises a mixture of (i) a solid particulate consisting essentially of at least 95% by weight of said hygroscopic plant growth regulator, and (ii) an effective amount between 0.2 to 3 parts by weight per 100 parts by weight of the plant growth regulator of an inert flow aid sufficient to inhibit hygroscopicity of said plant growth regulator.

12. The tablet of claim 11, wherein said plant growth regulator is an N,N-dimethyl-piperidinium salt.

13. The tablet of claim 11, wherein said plant growth regulator is selected from the group consisting of 1,1-dimethyl-3,4-dehydropiperidinium bromide, 4-chloro-1,1-dimethylpiperidinium bromide, 1,1-dimethyl-hexahydropyridazinium bromide, and 1,1-dimethylpiperidinium chloride.

14. The tablet as in claim 11, wherein the inert is selected from the group consisting of silicas, fumed silicas, precipitated silicas, aluminum silicates, magnesium silicates, zeolites, bentonites, montmorillonites, attapulgites, and mixtures thereof.

15. The tablet of claim 11, wherein said plant growth regulator is mepiquat chloride.

16. The tablet of claim 11, further including fillers, binders and/or disintegrants.

17. The tablet of claim 16, wherein the fillers, binders and/or disintegrants are selected from the group consisting of water-soluble cellulose derivatives, cellulose derivatives, carboxymethyl cellulose, hydroxypropyl methylcellulose, water-soluble plant gums, alignates, gelatin, polyvinylpyrrolidone, water-soluble starch, corn syrup, dextrin, pregelatinized starch which is at least partially soluble in water at ambient temperature, pregelatinized food starch, stable modified amylopectin, a low viscosity tapioca dextrin, dextrinized corn starch, maltodextrin microcrystalline cellulose, crosslinked polyvinyl pyrollidone, sodium carboxymethyl starch, and mixtures thereof.

18. The tablet of claim 16, wherein the fillers, binders and/or disintegrants include a carboxymethylcellulose.

19. The tablet as in claim 16, 17 or 18, wherein the fillers, binders and/or disintegrants are present in a ratio of the plant growth regulator to the fillers, binders and/or disintegrants of about 99.7:0.1.

20. The tablet as in claim 11, further including fillers, binders and/or disintegrants in a ratio of the plant growth regulator to the fillers, binders and/or disintegrants of about 99.7:0.1.

* * * * *